United States Patent [19]
Machek et al.

[11] Patent Number: 5,954,761
[45] Date of Patent: Sep. 21, 1999

[54] IMPLANTABLE ENDOCARDIAL LEAD ASSEMBLY HAVING A STENT

[75] Inventors: James E. Machek; Paul R. Spehr, both of Lake Jackson, Tex.

[73] Assignee: Intermedics Inc., Angleton, Tex.

[21] Appl. No.: 08/823,998

[22] Filed: Mar. 25, 1997

[51] Int. Cl.⁶ ...................................................... A61N 1/05
[52] U.S. Cl. .......................... 607/126; 607/122; 600/375; 600/381
[58] Field of Search ..................... 607/126, 116, 607/119, 122, 123, 124, 133–138; 600/372–375, 377, 378–381; 606/108, 129, 191, 192–199; 623/1

[56] References Cited

U.S. PATENT DOCUMENTS

| | | | |
|---|---|---|---|
| 5,099,838 | 3/1992 | Bardy | 128/419 |
| 5,111,811 | 5/1992 | Smits | 128/419 D |
| 5,314,430 | 5/1994 | Bardy | 607/5 |
| 5,423,772 | 6/1995 | Lurie et al. | 604/282 |

OTHER PUBLICATIONS

Ritter et al., "Four Chamber Pacing in Dilated Cardiomyopathy", PACE, Nov. 1994, vol. 17, pp. 1974–1979.

*Primary Examiner*—William E. Kamm
*Assistant Examiner*—Kennedy J. Schaetzle
*Attorney, Agent, or Firm*—Schwegman, Lundberg, Woessner & Kluth, P.A.

[57] ABSTRACT

Various endocardial lead assemblies are disclosed that may be particularly useful for placement within the coronary sinus. The lead assemblies may have open ends or closed ends. Lead assemblies having closed ends may be implanted using conventional implantation procedures. Lead assemblies have open ends may be implanted by first locating a stylet within the patient's body and, then, inserting the lead into the patient's body along the stylet. Each disclosed lead assembly uses one or more stents which expand to contact the inner surface of a body vessel once the lead has been properly positioned. Thus, the stents fix the lead at the desired location. Additionally, the stents may be used as electrodes for pacing and/or sensing.

26 Claims, 6 Drawing Sheets

FIG. 13

IMPLANTABLE ENDOCARDIAL LEAD ASSEMBLY HAVING A STENT

BACKGROUND OF THE INVENTION

1. Field of the Invention

The present invention relates generally to cardiac stimulation and, more particularly, to an implantable endocardial lead assembly having one or more stents.

2. Description of the Related Art

For a variety of reasons, a person's heart may not function properly and, thus, endanger the person's well-being. Medical devices have been developed to facilitate heart function. For instance, if a person's heart does not beat properly, a cardiac stimulator may be used to provide relief. A cardiac stimulator, such as a pacemaker or a cardioverter/defibrillator, is a medical device that delivers electrical stimulation to a patient's heart. A cardiac stimulator generally includes a pulse generator for creating electrical stimulation impulses and at least one conductive lead having an electrode at one end for delivering these electrical stimulation impulses to the designated portion of the heart.

There are generally two types of implantable leads used with cardiac stimulators. One type requires surgical opening of the patient's chest wall to expose the heart. The electrode is then attached to an outer portion of the heart. The other type of lead is inserted endoscopically through a body vessel, such as a vein, and directed into the heart. The distal end of the electrode is disposed within the heart near the myocardial tissue to be paced.

Existing endocardial leads have a lumen and an electrode having a closed tip coupled to the lead's distal end. Prior to transvenous insertion, a flexible stylet is disposed in the lumen so that the distal end of the stylet abuts the interior surface of the closed tip of the lead. The lead and the stylet are then inserted transvenously as a unit. The movement and positioning of the lead is accomplished by manipulating the proximal end of the stylet. After the distal end of the lead has been successfully positioned in or near the heart, the stylet is removed, and the proximal end of the lead is connected to a cardiac stimulator.

One or more leads may be positioned at various places in the heart, depending upon the type of pacing desired. Transvenous pacing of the left atrium and the left ventricle via the coronary sinus has become popular for both diagnosis and therapy of cardiac arrhythmias. The coronary sinus has five major venous tributaries that can be entered by pacing leads. The most common placement involves lodging the lead's electrode in the great cardiac vein. However, many patients require a more esoteric placement of the lead, such as, for example, in the anterior interventricular vein.

Lodging an electrode in a body vessel, such as the coronary sinus or one of its tributaries, can be quite difficult. This difficulty arises from the fact that most existing electrodes are designed to attach to an inner surface of a chamber of the heart, rather than the inner surface of a body vessel. Some leads, for instance, use electrodes that terminate in a corkscrew-shaped protuberance that is designed to screw into myocardial tissue. However, because this corkscrew is placed on the end of the electrode, it is difficult to attach it to walls of a body vessel that run parallel to the lead. By way of another example, some electrodes include angled tines that protrude radially from the electrode. Although these tines can often be used to lodge the electrode in a body vessel, the tines tend to occupy a significant amount of the flow path through the body vessel. As such, blood flow through the body vessel may be restricted.

There are also certain disadvantages associated with a lead having a closed end, particularly when placing the lead in the coronary sinus or one of its tributaries. Aside from the potential for venous occlusion, existing leads are implanted by the simultaneous manipulation of the lead and the stylet disposed within the lead. These leads may have diameters that begin to approach the diameters of the coronary sinus or its tributaries. Thus, such leads may be difficult to position by manipulating a stylet disposed therein. The difficulties of the implantation procedure may be further exacerbated by the presence of plaque or other obstructions in the coronary sinus or its tributaries.

The present invention is directed to overcoming, or at least reducing the effects of, one or more of the foregoing disadvantages.

SUMMARY OF THE INVENTION

In accordance with one aspect of the present invention, there is provided a lead assembly for implantation in a body vessel. The lead assembly includes a lead that has a conductor disposed therein. A stent is coupled to the conductor.

In accordance with another aspect of the present invention, there is provided a lead assembly for implantation in a body vessel. The lead assembly includes a lead that has a conductor disposed therein. An electrode is coupled to the conductor. A stent is coupled to the lead.

In accordance with yet another aspect of the present invention, there is provided a lead assembly for implantation in a body vessel. The lead assembly includes a lead that is adapted to transmit electrical signals. A stent is coupled to the lead. A sheath is disposed about the stent. The stent expands in response to removal of the sheath from the stent.

In accordance with still another aspect of the present invention, there is provided a lead assembly for implantation in a body vessel. The lead assembly includes an elongated lead that has a proximal end portion, a distal end portion, and a longitudinal axis. A conductor is disposed in the elongated lead. The conductor extends from the proximal end portion of the lead to the distal end portion of the lead. A stent, having a longitudinal axis, is disposed relative to the elongated lead with the longitudinal axis of the stent being substantially parallel to the longitudinal axis of the elongated lead. The stent is made of conductive material and is coupled to the conductor. The stent is radially expandable relative to its longitudinal axis.

In accordance with a further aspect of the present invention, there is provided a lead assembly for implantation in a body vessel. The lead assembly includes a lead that is adapted to transmit electrical signals. The improvement includes means for transmitting the electrical signals between the lead and the body vessel and for anchoring the lead within the body vessel.

In accordance with a yet further aspect of the present invention, there is provided a method for implanting in a body vessel a lead adapted to transmit electrical signals. The method includes the steps of (a) disposing the lead in the body vessel, and (b) expanding a stent on the lead to contact an inner surface of the body vessel.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
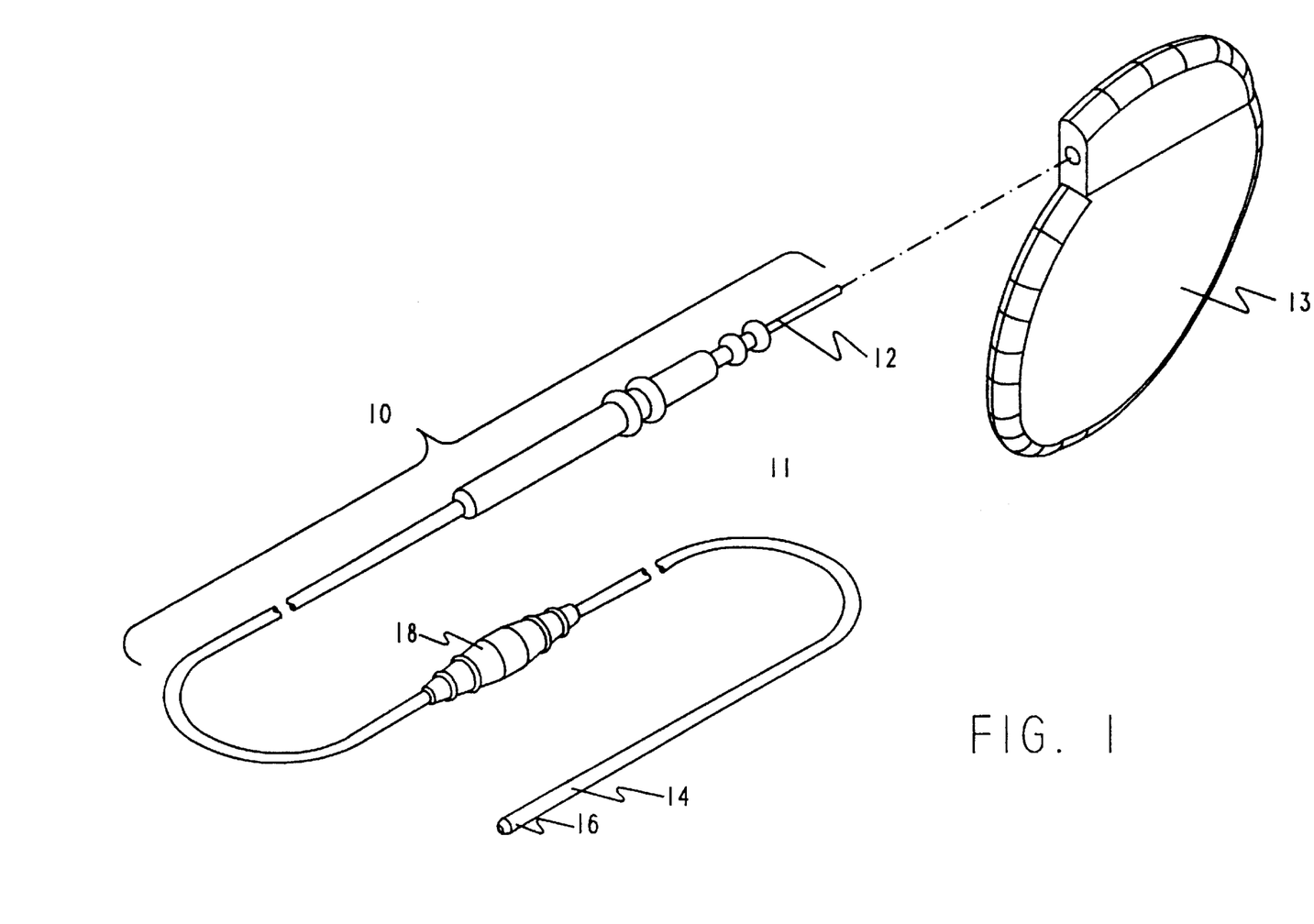
FIG. 1 illustrates an endocardial lead assembly and a cardiac stimulator.

Turning now to the drawings, FIG. 1 illustrates an endocardial lead assembly generally designated by a reference numeral 10. The lead assembly 10 is designed to be inserted endoscopically through a body vessel, such as the jugular vein, directly into the heart. The lead assembly 10 includes a lead 11 that has a proximal end 12 that may be coupled to a cardiac stimulator 13, such as, for example, a pacemaker or cardioverter/defibrillator. A lead such as a thinline 430-10, 430-20, or 431-11, available from the assignee, may be used. The distal end 14 of the lead 11 is attached to an electrode assembly 16. A suture sleeve 18 is slidably disposed on the lead 11. The suture sleeve 18 may be attached to the insertion vein of a patient in a conventional manner.

Figure 2:
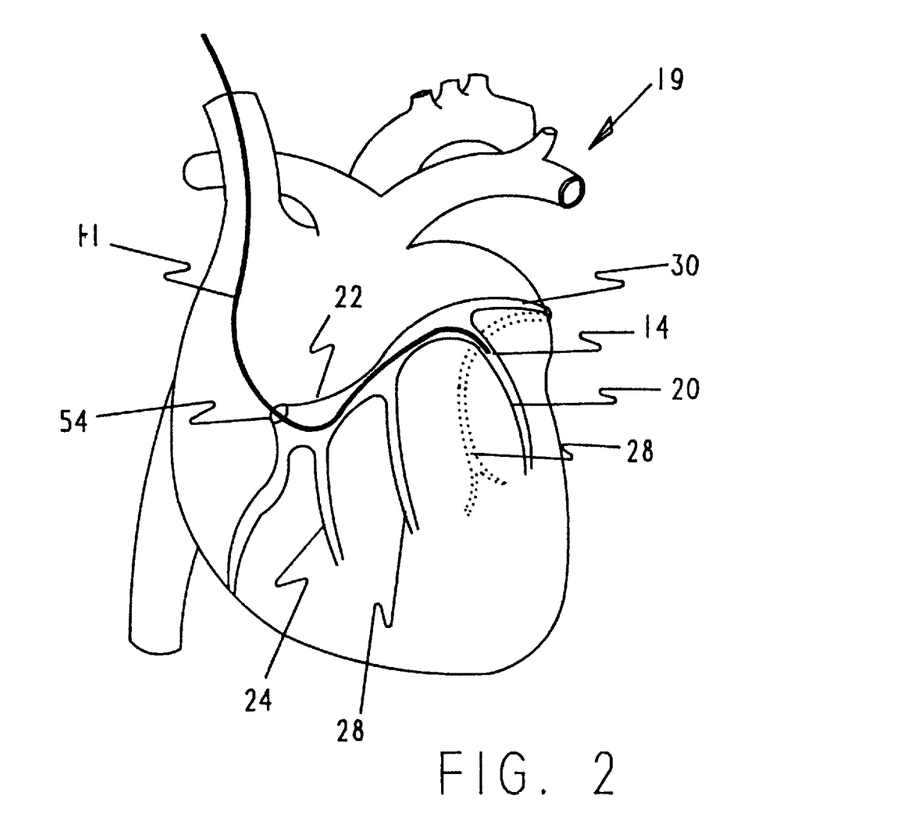
FIG. 2 illustrates an anterior view of a human heart.

The lead assembly 10 is designed to be placed within a human heart 19 as illustrated in FIG. 2. The distal end 14 of the lead 11 is shown implanted in the left diagonal vein tributary 20 of the coronary sinus 22. The lead 11 may also be placed in the coronary sinus 22 or in one of the other coronary sinus tributaries, such as the left post interventricular vein 24, the obtuse marginal vein 26, the anterior interventricular vein 28, or the great cardiac vein 30.

Figure 3:
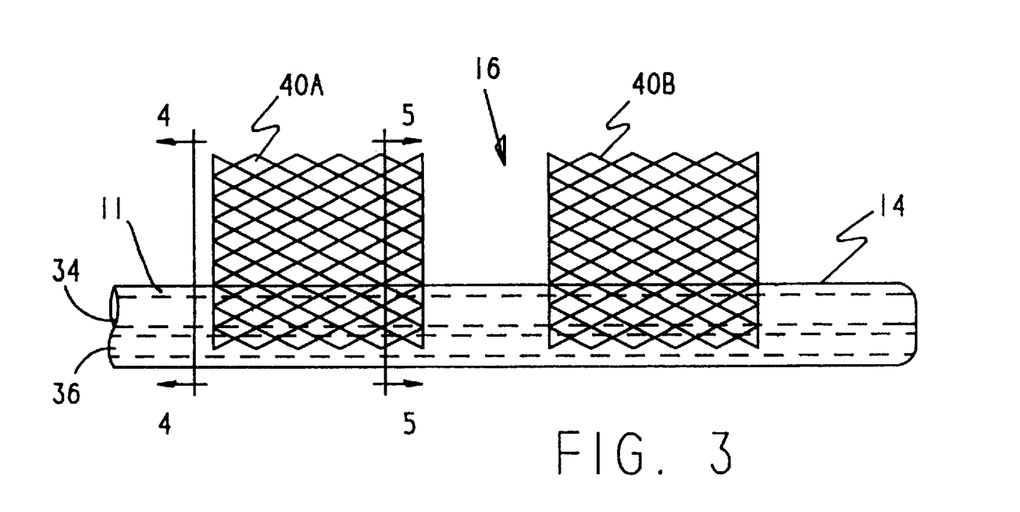
FIG. 3 illustrates a side view of a first embodiment of the lead assembly of FIG. 1.
Figure 4:
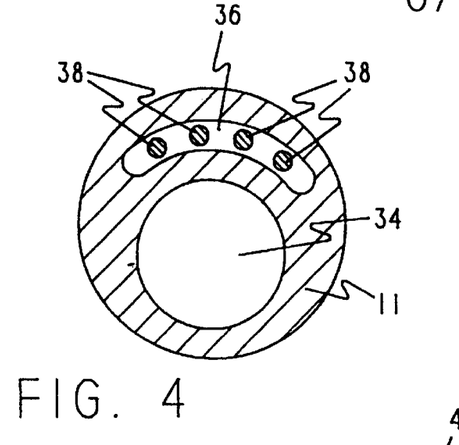
FIG. 4 illustrates an inverted cross-sectional view taken along line 4—4 in FIG. 3.

To facilitate placement of the lead 11 within the heart 19, as well as longevity of the lead 11 during subsequent use, the lead 11 is flexible. The lead 11 is composed of a flexible biocompatible material, such as, for example, silicone or polyurethane. Referring to FIGS. 3 and 4, the lead 11 contains a main lumen 34 that extends along the length of the lead 11. The lead 11 also includes a secondary lumen 36 that extends substantially along the length of the lead 11. One or more flexible conductors 38, such as coiled conductors, are disposed in the secondary lumen 36. The conductors 38 are coupled to the cardiac stimulator 13 at the proximal end 12 of the lead assembly 10 for transmitting electrical impulses to and from the electrode assembly 16. The conductors 38 may be, for instance, drawn filled tubing (DFT), where the tube is composed of MP35N and filled with silver, or the conductors 38 may be drawn brazed strand (DBS). The conductors 38 may also be coated with an insulating material, such as polyethylene tetrafluoride, polyimide, ETFE, or other suitable biocompatible insulating materials.

As illustrated in FIG. 3, the electrode assembly 16 includes two stents 40a and 40b. Also referring to FIG. 5, it can be seen that the stents 40a and 40b are a generally cylindrical arrangement of interwoven wire mesh. The stents 40a and 40b may be self-expanding, or they may be expanded using balloons (not shown). As will be explained in greater detail below, the stents 40a and 40b may be used as electrically conductive electrodes, or one or both of the stents 40a and 40b may merely be used to locate and lodge the distal end 14 of the lead 11 within a body vessel.

If one or both of the stents 40a and 40b are used as electrodes, at least a portion of the wire mesh that makes up each stent 40a and 40b remains uncoated. A portion of each stent 40a and 40b may be coated with an electrically insulative material, such as polyurethane, ETFE, paralene or another suitable biocompatible material, in order to control the amount of electrical contact that each stent 40a and 40b makes with the tissue of the body vessel.

The use of a stent 40a or 40b as an electrode provides several advantages as compared with traditional electrodes. First, the small surface area of a stent 40a or 40b as compared with existing electrodes provides a higher impedance that may extend the life of the battery which powers the cardiac stimulator 13. Second, because the stents 40a and 40b may be capable of expanding to a size greater than the diameter of the body vessel, the stents 40a and 40b provide a more reliable and better electrical contact than many existing electrodes. Third, the stents 40a and 40b serve the dual functions of supplying electrical impulses carried by the conductors 38 to the tissue, as well as acting as the structure for retaining the distal end 14 of the lead assembly 10 at the selected position.

Although any suitable stent may be used, stents available from the Schneider Corporation may be particularly advantageous, although such stents may be modified before use in this application by trimming them to the proper size. Also, to enhance the electrical contact between the stents 40a and 40b and the myocardial tissue, the stents 40a and 40b may be coated with a suitable conductivity enhancing material, such as iridium oxide or titanium nitride.

As illustrated in FIG. 4, the use of a number of conductors 38 rather than a single conductor may be advantageous because multiple conductors typically provide lower impedance than a single conductor. Also, the multiple conductors facilitate the multiple pacing and/or sensing functions provided by the cardiac stimulator 13. One or more of the conductors 38 is attached to one or more of the wires that comprise the stent 40a or 40b so that the stent may be used as an electrode for pacing and/or sensing. The connection between the conductors 38 and the wires of the stents 40a and 40b may be made, for instance, by welding them together using a laser.

Figure 5:
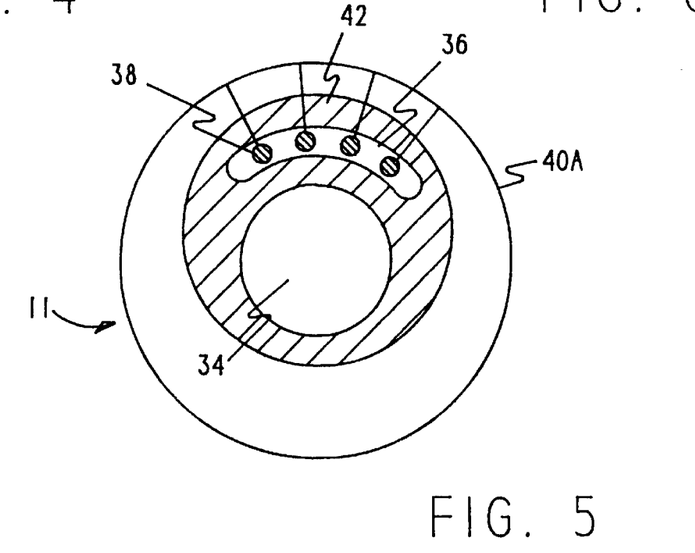
FIG. 5 illustrates an inverted cross-sectional view taken along line 5—5 of FIG. 3.

As illustrated in FIGS. 3, 4, and 5, the stents 40a and 40b are coupled to conductors 38 that reside in the secondary lumen 36 that is offset from the main lumen 34. The wires of the stents 40a and 40b are coupled to the conductors 38 contained within the secondary lumen 36 directly through the wall 42 between the outer periphery of the lead 11 and the radially outward inner surface of the secondary lumen 36.

Figure 12:
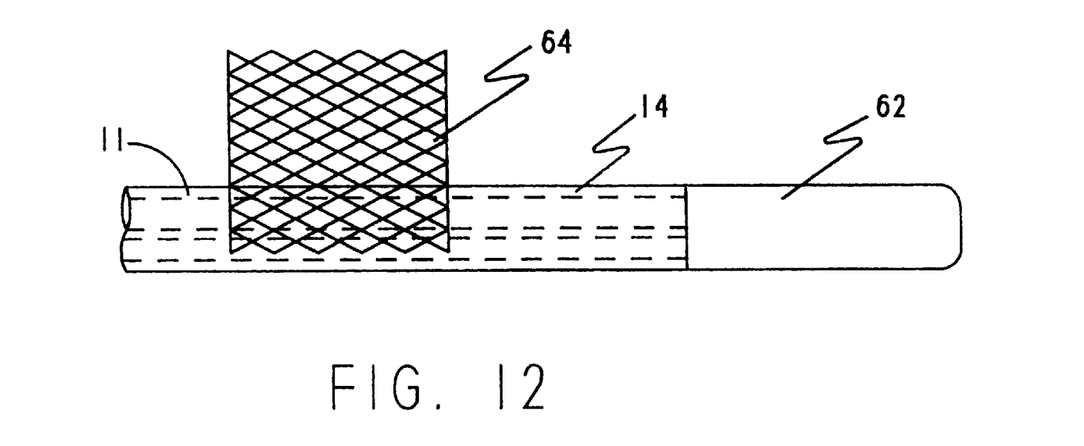
FIG. 12 illustrates a fourth embodiment of the lead assembly of FIG. 1.

The stents 40a and 40b may surround the lead 11, they may partially surround the lead 11, or they may be coupled to the surface of the lead. In the latter two instances, when the stents 40a and 40b expand, they urge the lead 11 against the opposite wall of the body vessel in which the lead assembly 10 is inserted. This design may be particularly advantageous if one or both of the stents 40a and 40b is used only as a means for fixing the distal end 14 of the lead assembly 10 within the body vessel where the electrode is coupled to the distal end 14 of the lead assembly 10, as illustrated in FIG. 12 to be discussed in greater detail below.

Figure 6:
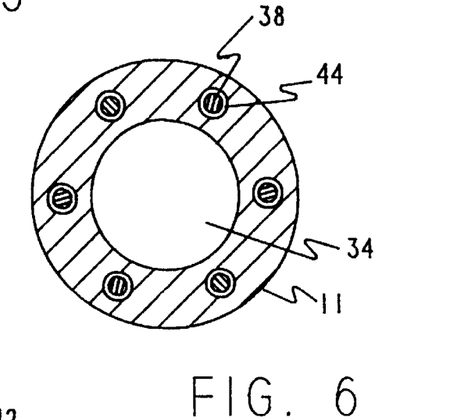
FIG. 6 illustrates a cross-sectional view of an alternate embodiment taken along line 4—4 of FIG. 3.

The lead 11 may be configured differently from the embodiment illustrated in FIGS. 3, 4, and 5. For instance, FIG. 6 illustrates a lead 11 having a plurality of conductors 38 disposed in individual lumens 44 arranged in a symmetrical fashion close to the outer periphery of the lead 11 and surrounding the main lumen 34. While in either configuration it is possible to position the stents 40a and 40b in an offset manner as illustrated in FIG. 3, it is also possible to position the stents 40a and 40b so that they surround or are concentric with the lead 11. Because the conductors 38 are disposed symmetrically near the periphery of the lead 11 illustrated in FIG. 6, it may be easier to dispose the stents 40a and 40b concentrically about the lead 11 with a symmetrical conductor arrangement.

Figure 7:
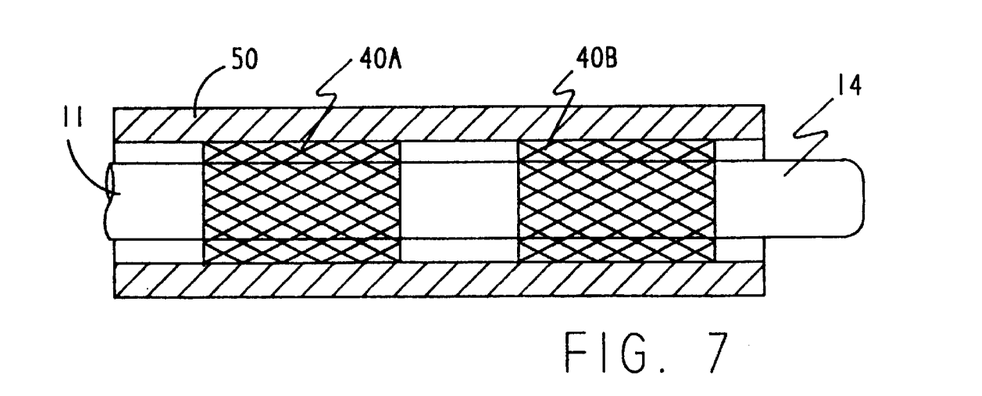
FIG. 7 illustrates a cross-sectional view of a retaining sleeve placed on a second embodiment of the lead assembly of FIG. 1.

To insert the lead assembly 10 into a patient's body vessel, a sheath 50 is placed about the stents 40a and 40b. The sheath 50 is designed to prevent the stents 40a and 40b from expanding until the distal end 14 of the lead 11 has been properly located within the patient's body vessel. The sheath 50 is advantageously made of a biocompatible material, such as polyurethane or nylon. Once the distal end 14 of the lead 11 has been properly located, the sheath 50 may be withdrawn from the patient to permit the stents 40a and 40b to expand and, thus, fix the distal end 14 of the lead 11 at the desired location.

As an alternative to the removable sheath 50 discussed above, the sheath 50 may be a coating of dissolvable biocompatible material that covers the stents 40a and 40b to prevent them from expanding until the distal end 14 of the lead 11 has been properly located within a patient's body vessel. In this case, the sheath 50 may be made of PEG or sugar, for instance. This embodiment has certain advantages and disadvantages as compared with the previously discussed embodiment. The dissolvable coating is advantageous because it does not require that the physician physically remove the sheath 50 during the implantation procedure, thus allowing the implantation procedure to be completed more quickly. However, this embodiment may be disadvantageous as compared with the previous embodiment because the dissolvable sheath 50 must be inserted and properly located within the patient's body vessel before the material dissolves. Once the sheath 50 dissolves, the stents 40a and 40b expand and contact the inner surface of the body vessel. Hence, it may be difficult to position the distal end 14 of the lead 11 once the stents 40a and 40b have expanded.

If the stents 40a and 40b are of the balloon expandable type, the sheath 50 may be omitted during the implantation procedure. Thus, once the distal end 14 of the lead 11 has been properly located within the body vessel 20, the balloons (not shown) may be inflated to expand the stents 40a and 40b to contact the inner surface of the body vessel 20.

The distal end 14 of the lead 11 may be closed so that the lead assembly 10 may be implanted using a conventional implantation procedure. In a conventional procedure, a stylet (not shown) is inserted into the lumen 34. The distal end 14 of the lead 11 is then inserted into a patient's body vessel. The proximal end of the stylet is manipulated to direct the lead assembly 10 through the body vessel until the distal end 14 reaches the desired location. The stylet is then removed, leaving the lead assembly 10 within the patient's body vessel. Once the sheath 50 is removed, the proximal end of the lead 11 may be coupled to the cardiac stimulator 13.

Figure 8:
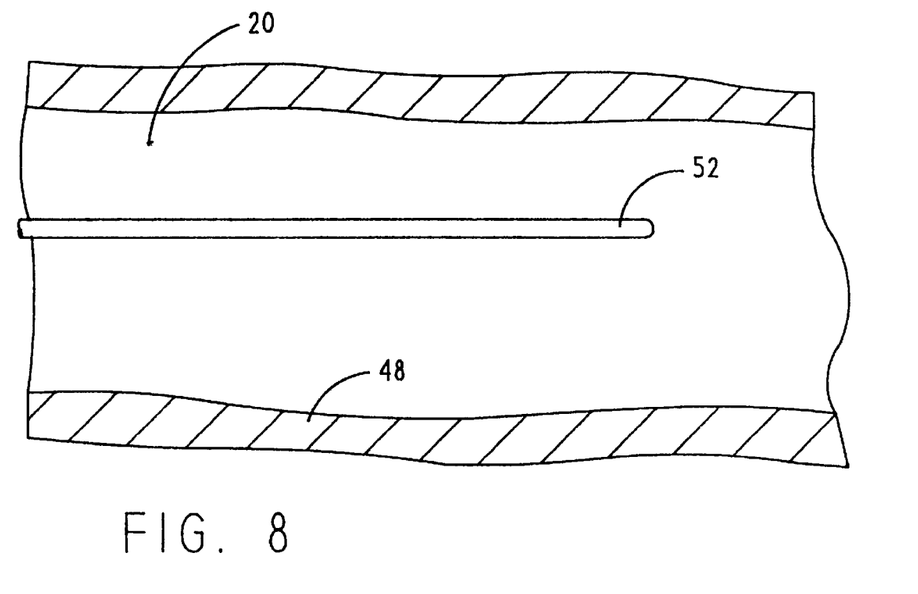
FIG. 8 illustrates a stylet inserted in a body vessel of the heart of FIG. 2.

Although a conventional implantation procedure, as described above, may be used in many circumstances, accurate placement of the distal end 14 in the coronary sinus 22 or one of its tributaries may be difficult to accomplish using such conventional procedures. Therefore, it may be advantageous to provide a lead 11 having an open distal end 14. To implant an open-ended lead, a guide wire or stylet 52 is inserted into a patient's body vessel 20 and manipulated to place the distal end of the stylet 52 at a desired location in the body vessel 20, as illustrated in FIG. 8. The coronary sinus 22 is commonly entered from a vein on the left side of a person's body, such as the cephalic or subclavian (not shown). Hence, the stylet 52 is inserted into the appropriate body vessel and manipulated, usually with the aid of fluoroscopy, until it reaches the heart. As illustrated in FIG. 2, following transvenous insertion of the stylet 52 into the right atrium of the heart, the stylet 52 is manipulated to avoid the tricuspid valve (not shown) and enter the coronary sinus ostium 54. Longitudinal force is then applied to the stylet 52 to advance the distal end of the stylet 52 into the desired tributary of the coronary sinus 22, in this case the left diagonal vein 20. Fluoroscopy may be used to confirm the proper positioning of the stylet 52. Lateral fluoroscopy may be helpful in confirming the typical posterior location of the stylet 52 in the coronary sinus 22 that is different from an anteriorly directed pulmonary artery position.

Because the diameter of the stylet 52 is much smaller than the diameter of the lead 11, it is easier to position the stylet 52 within a body vessel as compared with a lead and stylet combination. This is particularly true in body vessels such as the coronary sinus 22 or one of its tributaries where the body vessel 20 may have a small diameter or a constriction 48.

Figure 9:
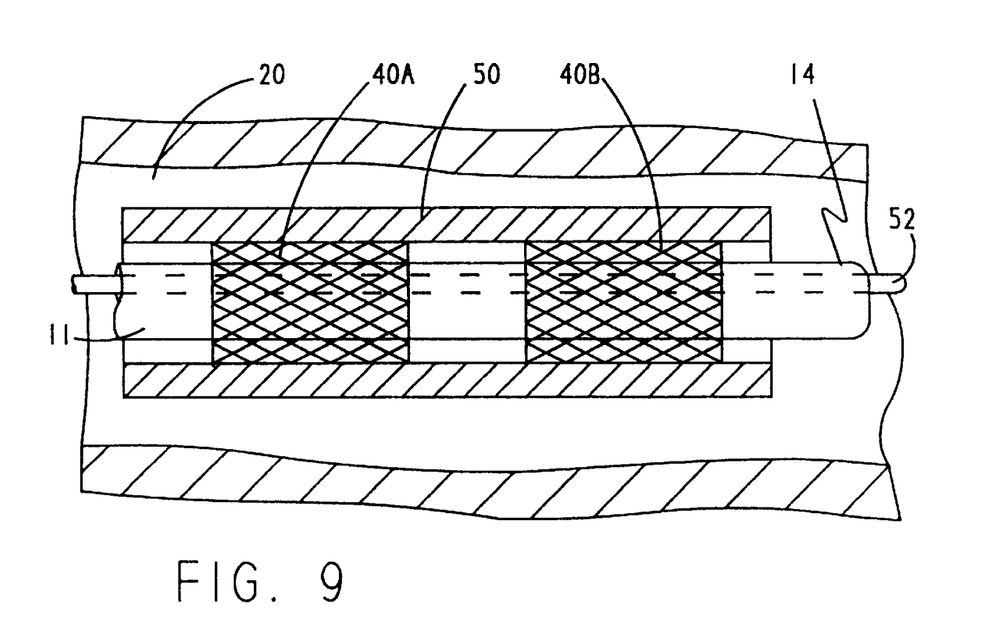
FIG. 9 illustrates the lead assembly and retaining sleeve of FIG. 7 inserted within a body vessel of the heart of FIG. 2 along the stylet illustrated in FIG. 8.

Once the stylet 52 has been properly positioned, as illustrated in FIG. 8, the lumen 34 at the distal end 14 of the lead 11 is placed over the proximal end (not shown) of the stylet 52. The distal end 14 of the lead 11 is then advanced along the stylet 52 until the distal end 14 of the lead 11 reaches the desired position within the left diagonal vein 20, or other body vessel, as illustrated in FIG. 9. Because the lead 11 follows the previously inserted stylet 52, insertion of the lead 11 typically proceeds easier and faster as compared with conventional implantation methods. After the lead 11 has been properly positioned, the stylet 52 is withdrawn from the body leaving the lead 11 in place as shown in FIG. 2.

Figure 10:
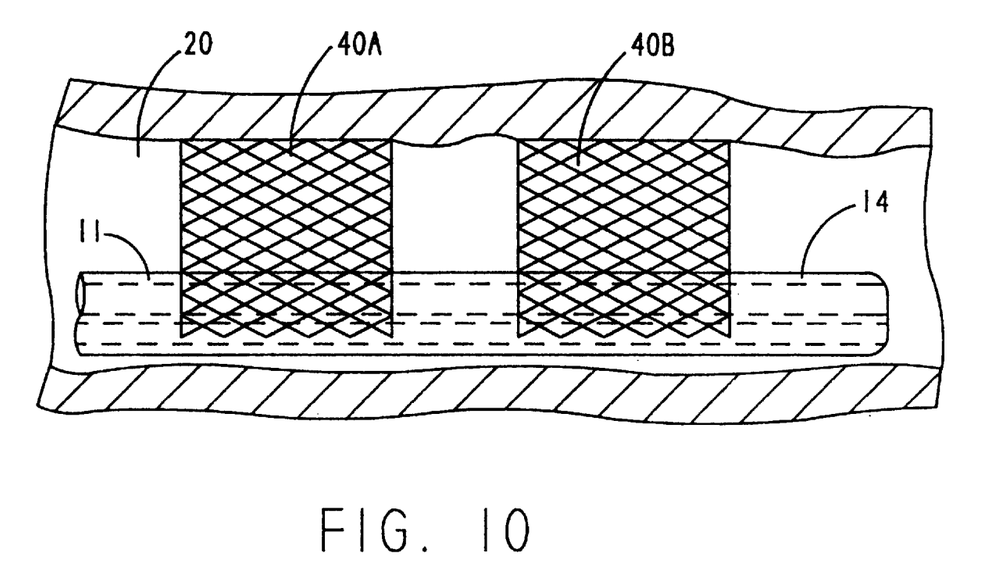
FIG. 10 illustrates the lead assembly of FIG. 3 inserted within a body vessel of the heart of FIG. 2.

The sheath 50 may be removed before or after the stylet 52 is removed. Once the sheath 50 is removed, the stents 40a and 40b expand to contact the walls of the body vessel, as illustrated in FIG. 10, and, thus, hold the distal end 14 of the lead 11 in place. Because the expanded stents 40a and 40b anchor the distal end 14 of the lead 11 within the body vessel 20, it may be advantageous to remove the stylet 52 from the lead 11 after the sheath has been removed.

The embodiment of the lead assembly 10 discussed thus far includes the two stents 40a and 40b. As previously discussed, one or both of the stents 40a and 40b may be used as electrodes, or one or both stents 40a and 40b may be used merely as a means for fixing the distal end 14 of the lead 11 at a desired location within the patient's body vessel 20. If both of the stents 40a and 40b are used as electrodes, as well as a means for fixing the distal end 14 of the lead 11 within the body vessel 20, the stent 40a may be used to pace and/or sense the atrium, and the stent 40b may be used to pace and/or sense the ventricle.

Figure 11:
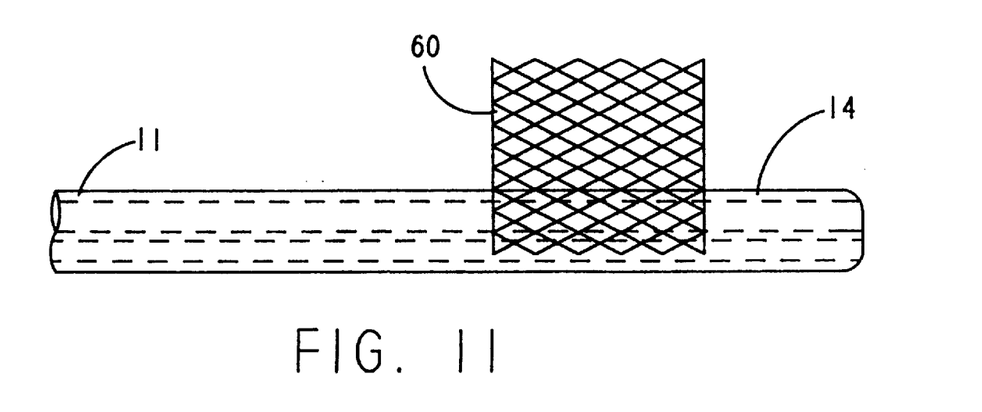
FIG. 11 illustrates a third embodiment of the lead assembly of FIG. 1.

Other embodiments of the lead assembly 10 may also include stents used for various purposes. For instance, FIG. 11 illustrates a lead 11 having a single stent 60 located at the distal end 14 of the lead 11. The single stent 60 may be an electrode used for unipolar pacing and/or sensing. By way of another example, FIG. 12 illustrates a lead 11 having a conventional electrode 62 located at the distal end 14 of the lead 11. A stent 64 is also located proximate the distal end 14 of the lead 11. The stent 64 fixes the distal end 14 of the lead 11 at the desired location when the stent 64 is expanded within the patient's body vessel. The stent 64 also serves to urge the electrode 62 against the wall of the body vessel to facilitate a good electrical contact between the electrode 62 and the body vessel. Additionally, the stent 64 may be used as a second electrode. For instance, the stent 64 may be located in the coronary sinus 22 for pacing and/or sensing, while the electrode 62 may be located in the great cardiac vein 30 for pacing and/or sensing the left ventricle.

Figure 13:
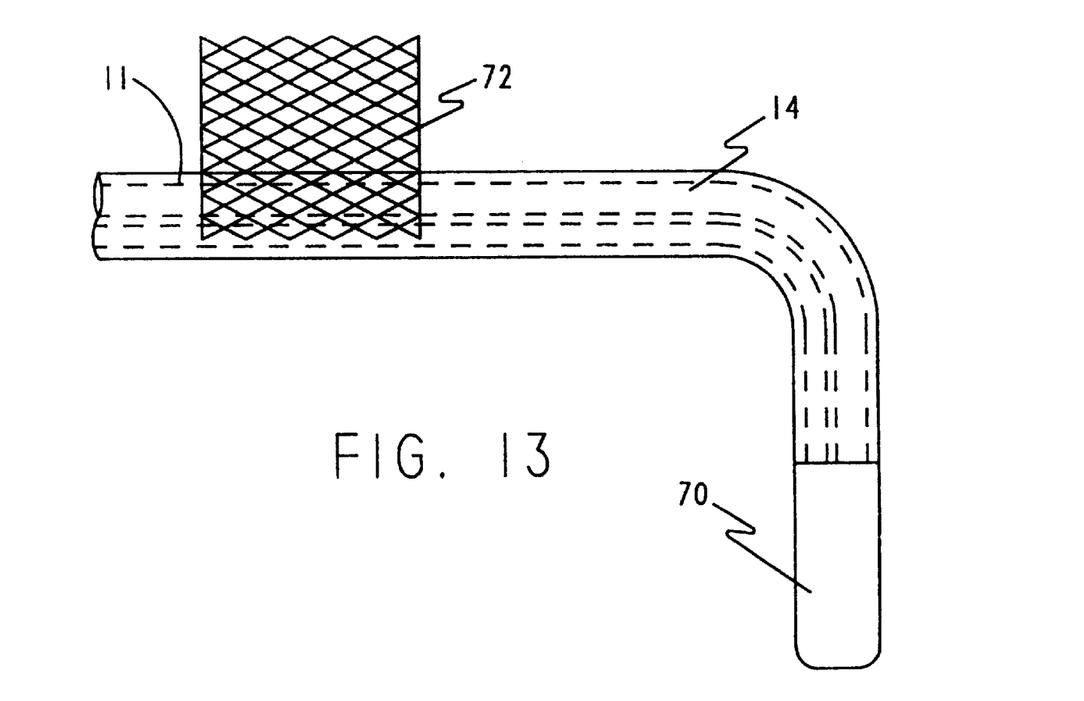
FIG. 13 illustrates a fifth embodiment of the lead assembly of FIG. 1.

FIG. 13 illustrates yet another embodiment of the lead assembly 10. In this embodiment, and electrode 70 is coupled to the distal end 14 of the lead 11. A stent 72 is coupled to the lead 11 between the lead's proximal and distal ends. The stent 72 may be used to fix the location of the lead 11 when it expands to contact the inner surface of the body vessel in which it is placed. The stent 72 may also act as an electrode. For instance, the stent 72 may be placed in the coronary sinus 22, while the electrode 70 extends into the great cardiac vein 30 for pacing and/or sensing the left ventricle.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A lead assembly for implantation in a body vessel, comprising:
    a lead having a conductor disposed therein; and
    a stent being coupled to said conductor and partially surrounding a portion of said lead.

2. The lead assembly, as set forth in claim 1, further comprising:
    means for controllably expanding said stent.

3. The lead assembly, as set forth in claim 2, wherein said means comprises:
    a sheath being disposed about said stent, said stent expanding in response to removal of said sheath from said stent.

4. The lead assembly, as set forth in claim 1, wherein said lead comprises a proximal end portion and a distal end portion, said stent being coupled to said conductor at said distal end portion of said lead.

5. The lead assembly, as set forth in claim 1, wherein said lead comprises a flexible member that houses said conductor.

6. The lead assembly, as set forth in claim 5, wherein said flexible member comprises a proximal end and a distal end, and wherein said flexible member further comprises a lumen extending from said proximal end portion to said distal end portion, said lumen being sized to accept a stylet.

7. The lead assembly, as set forth in claim 6, wherein said lumen extends through said distal end portion to form an opening therein.

8. A lead assembly for implantation in a body vessel, comprising:
    a lead having a conductor disposed therein;
    an electrode being coupled to said conductor; and
    a stent being coupled to said lead. and partially surrounding a portion of said lead.

9. The lead assembly, as set forth in claim 8, further comprising:
    means for controllably expanding said stent.

10. The lead assembly, as set forth in claim 9, wherein said means comprises:
    a sheath being disposed about said stent, said stent expanding in response to removal of said sheath from said stent.

11. The lead assembly, as set forth in claim 8, wherein said lead comprises a proximal end portion and a distal end portion, said stent being coupled to said lead proximate said distal end portion of said lead.

12. The lead assembly, as set forth in claim 8, wherein said lead comprises a flexible member that houses said conductor.

13. The lead assembly, as set forth in claim 12, wherein said flexible member comprises a proximal end and a distal end, and wherein said flexible member further comprises a lumen extending from said proximal end to said distal end, said lumen being sized to accept a stylet.

14. The lead assembly, as set forth in claim 13, wherein said lumen extends through said distal end to form an opening therein.

15. The lead assembly, as set forth in claim 8, wherein said stent is coupled to said conductor.

16. A lead assembly for implantation in a body vessel, comprising:
    a lead being adapted to transmit electrical signals;
    a stent being coupled to said lead and partially surrounding a portion of said lead; and
    a sheath disposed about said stent, said stent expanding in response to removal of said sheath from said stent.

17. The lead assembly, as set forth in claim 16, wherein said lead comprises a proximal end portion and a distal end portion, said stent being coupled to said distal end portion of said lead.

18. The lead assembly, as set forth in claim 16, wherein said lead comprises a flexible member of biocompatible material that houses a conductor.

19. The lead assembly, as set forth in claim 18, wherein said conductor comprises an electrically insulative coating of biocompatible material.

20. The lead assembly, as set forth in claim 18, wherein said stent is coupled to said conductor.

21. The lead assembly, as set forth in claim 16, wherein said lead comprises a proximal end portion and a distal end portion, and wherein said lead further comprises a lumen extending from said proximal end portion to said distal end portion, said lumen being sized to accept a stylet.

22. The lead assembly, as set forth in claim 21, wherein said lumen extends through said distal end portion to form an opening therein.

23. A lead assembly for implantation in a body vessel, comprising:

an elongated lead having a proximal end portion, a distal end portion, and a longitudinal axis;

a conductor disposed in said elongated lead and extending from said proximal end portion of said lead to said distal end portion of said lead; and a stent having a longitudinal axis, said stent being disposed relative to said elongated lead with the longitudinal axis of said stent being substantially parallel to the longitudinal axis of said elongated lead, said stent being comprised of conductive material and being-coupled to said conductor, said stent being radially expandable relative to its longitudinal axis and partially surrounding a portion of said lead.

24. In a lead assembly for implantation in a body vessel, wherein said lead assembly comprises a lead being adapted to transmit electrical signals, the improvement comprising:

means for transmitting said electrical signals between said lead and said body vessel and a stent coupled to said lead and partially surrounding a portion of said lead for anchoring said lead within said body vessel.

25. The lead assembly, as set forth in claim 24, wherein said stent is partially coated with biocompatible material.

26. The lead assembly, as set forth in claim 24, wherein said stent expands to contact said body vessel.

* * * * *